United States Patent [19]
Casarcia et al.

[11] Patent Number: 5,515,728
[45] Date of Patent: May 14, 1996

[54] ULTRASONIC FIXTURE ASSEMBLY FOR HOLDING MULTIPLE ULTRASONIC TRANSDUCERS

[75] Inventors: Dominick A. Casarcia, Cincinnati, Ohio; William F. Jackson, Dry Ridge, Ky.

[73] Assignee: General Electric Company, Cincinnati, Ohio

[21] Appl. No.: 405,103

[22] Filed: Mar. 16, 1995

Related U.S. Application Data

[62] Division of Ser. No. 112,728, Aug. 26, 1993, Pat. No. 5,421,200.

[51] Int. Cl.⁶ .................................................. G01N 29/04
[52] U.S. Cl. ........................................................... 73/623
[58] Field of Search ............................ 73/596, 598, 623, 73/625, 629, 632, 634, 655

[56] References Cited

U.S. PATENT DOCUMENTS

| | | | |
|---|---|---|---|
| 3,289,468 | 12/1966 | Van Der Veer et al. | 73/637 |
| 3,573,515 | 4/1971 | Stombaugh | 310/336 |
| 3,990,300 | 11/1976 | Kossoff | 73/640 |
| 4,112,775 | 9/1978 | Sylvester et al. | 73/627 |
| 4,674,334 | 6/1987 | Chimenti et al. | 73/627 |
| 4,852,577 | 8/1989 | Smith et al. | 128/660.07 |
| 4,862,748 | 9/1989 | Woodmansee | 73/641 |
| 5,007,291 | 4/1991 | Walters et al. | 73/640 |
| 5,062,300 | 11/1991 | Vallee | 73/623 |
| 5,062,301 | 11/1991 | Aleshin et al. | 73/629 |
| 5,107,709 | 4/1992 | McCarty | 73/655 |

*Primary Examiner*—Hezron E. Williams
*Assistant Examiner*—Christine K. Oda
*Attorney, Agent, or Firm*—Andrew C. Hess; David L. Narciso

[57] ABSTRACT

An ultrasonic fixture assembly for holding multiple ultrasonic transducers includes a mounting support rod for attaching the fixture assembly to a manipulator of a ultrasonic inspection system. A plurality of transducer mounting blocks may be mounted to the support rod by an elongated mounting bar or a single transverse mounting block may be mounted to the support rod. Each of the transducer mounting blocks will have a channel formed therein for slidably receiving an ultrasonic transducer or if a single transverse mounting block is used a plurality of channels will be formed through the mounting block. A central channel or a central transducer mounting block is provided for receiving and retaining a longitudinal wave type ultrasonic transducer and other channels or transducer mounting blocks disposed on either side of the longitudinal transducer are formed to hold shearwave type transducers. The shear transducer mounting blocks are pivotably mounted to the elongated support rod to permit positioning the transducers to provide a predetermined angle of incidence of the ultrasonic signal. A mechanism is also provided to permit adjustment of the water path length between the transducer and the surface of the workpiece.

2 Claims, 5 Drawing Sheets

ULTRASONIC FIXTURE ASSEMBLY FOR HOLDING MULTIPLE ULTRASONIC TRANSDUCERS

The government has rights in this invention pursuant to Contract No. F33657-85-C-2147 awarded by the Department of Air Force.

This application is a division of application Ser. No. 08/112,728, filed Aug. 26, 1993, U.S. Pat. No. 5,421,200.

BACKGROUND OF THE INVENTION

The present invention relates to ultrasonic inspection of workpieces and, more particularly, to a fixture assembly for holding multiple ultrasonic transducers to provide substantially complete ultrasonic inspection of a portion of a workpiece in a single scanning operation or in a minimum number of scans to improve throughput and inspection efficiency.

Typically, an ultrasonic inspection will involve a single transducer mounted to an ultrasonic inspection system manipulator. This single transducer, however, will inject or introduce ultrasonic energy or sound waves into a workpiece under inspection only in one direction and also receive a return or reflected signal or sound waves from a flaw or defect along this same direction. For example, a longitudinal ultrasonic wave is typically introduced into the workpiece along a path normal to the workpiece surface by a transducer and the transducer will receive return ultrasonic energy along this same normal path. Therefore, flaws or defects which are oriented substantially parallel to the workpiece surface will be easily detected; however, flaws or defects which are not oriented substantially parallel to the workpiece surface, such as flaws oriented diagonally or substantially vertical relative to the workpiece surface, may be missed or deemed insignificant because the defect or flaw is only inspected from one direction and may appear small and insignificant in this direction.

Ultrasonic inspection from one direction or perspective, normal to the workpiece surface, may be adequate for some workpieces; however, for those components requiring a more complete and thorough inspection, it may be desirable to introduce or inject a shearwave ultrasonic signal into the workpiece at a predetermined angle of incidence to provide a desired angle of refraction of the ultrasonic energy upon entering the workpiece. As many as three or more separate ultrasonic scans may then be required to substantially completely inspect a workpiece. A longitudinal ultrasonic inspection scan is performed to pick up those flaws or defects oriented substantially parallel to the workpiece surface and at least two circumferential shearwave ultrasonic inspection scans may be required to pick up those flaws or defects which may be oriented substantially vertical or at some angle relative to the surface of the workpiece.

Phased array transducers are available for performing longitudinal and shearwave inspections in a single scan; however, these phased array transducers are more expensive than a single conventional transducer and if a single element of the array fails or goes bad, the entire phased array must be replaced rather than replacing a single transducer.

It is accordingly a primary object of the present invention to provide a novel fixture assembly for holding multiple ultrasonic transducers to provide substantially complete ultrasonic inspection of a workpiece in a single scanning operation or in a minimum number of required scanning operations.

It is another object of the present invention to provide a novel ultrasonic fixture assembly for holding multiple conventional ultrasonic transducers such that if one transducer fails or goes bad, only that single bad transducer need be replaced.

It is a further object of the present invention to provide a novel ultrasonic fixture assembly for holding multiple conventional ultrasonic transducers which is usable with conventionally known immersion type ultrasonic inspection systems and can be easily attached or detached from the manipulators of such systems.

These and other objects of the present invention, together with the features and advantages thereof, will become apparent from the following specification when read with the accompanying drawings.

SUMMARY OF THE INVENTION

In accordance with the present invention, an ultrasonic fixture assembly for holding multiple ultrasonic transducers includes an elongated mounting bar and a central transducer mounting block or receptacle mounted in a central location of the elongated mounting bar. The central transducer mounting block has a first channel formed therein for receiving a longitudinal wave type ultrasonic transducer. At least one shear transducer mounting block or receptacle is pivotably mounted to the elongated mounting bar on each side of the central transducer mounting block. Each of the shear transducer mounting blocks has a channel formed therein for slidably receiving a shearwave type ultrasonic transducer, and each of the shear transducer mounting blocks is pivotably mounted to the elongated mounting bar to permit positioning of the shear transducer mounting block and the shearwave transducer disposed therein to provide a refracted shearwave at a predetermined angle of refraction within a workpiece under inspection. An adjustment means is associated with each shear transducer mounting block for slidably adjusting the position of the shearwave transducer within the channel, formed in the transducer mounting block, to permit positioning the shearwave transducer at a predetermined water path length between the transducer and the workpiece under inspection for focusing ultrasonic energy or sound waves from the shearwave transducer at a desired location within the workpiece. The ultrasonic fixture assembly further includes means for attaching the assembly to a manipulator of an immersion type ultrasonic inspection system.

In another embodiment of the present invention for performing an ultrasonic inspection of a bore or hub, such as a bore formed in the center of a disk of a gas turbine engine, includes a central support rod for attaching the fixture assembly to an immersion type ultrasonic inspection manipulator. A support member is attached at one end to the support rod and has a plurality of uniformly, circumferentially spaced openings formed therein, each for receiving a respective ultrasonic transducer. A plurality of tubes are each slidably received in a respective one of the plurality of openings at an end of the support member opposite to the one end attached to the support rod. One end of each of the plurality of tubes is coupled to an operating face of an associated one of the ultrasonic transducers and a distal end of each of the plurality of tubes has a mirror or reflective means mounted therein for reflecting ultrasonic energy from the associated ultrasonic transducer at a predetermined angle into the workpiece under inspection. A central tube is mounted to the support member for receiving a central ultrasonic transducer. The central tube has a centerline in alignment with a centerline of the central support rod and the support member. The center transducer is used to align the fixture in the workpiece to be inspected to position each mirror or reflective device at an equal distance from the workpiece.

DETAILED DESCRIPTION OF THE PREFERRED EMBODIMENTS

Figure 1:
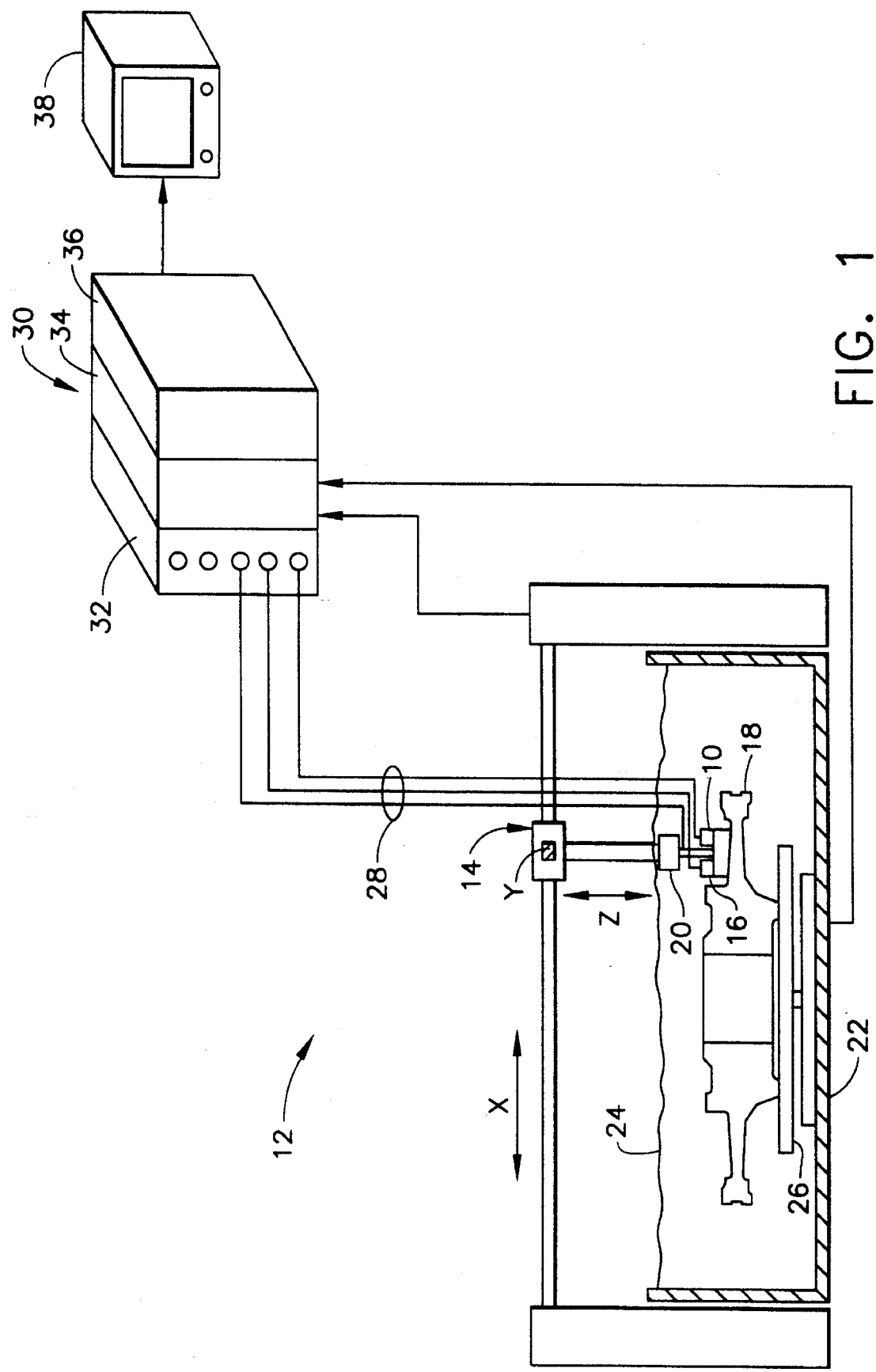
FIG. 1 is a schematic diagram of a typical ultrasonic inspection system with which the ultrasonic fixture assembly of the present invention may be used.

Referring initially to FIG. 1, the ultrasonic fixture assembly 10 for holding multiple ultrasonic transducers may be used in conjunction with an immersion type ultrasonic inspection system 12. The ultrasonic inspection system 12 includes a manipulator 14 to which the fixture assembly 10 is releasably attachable. The manipulator 14 includes X, Y and Z axes of motion to permit movement or scanning of the ultrasonic fixture assembly 10 and the ultrasonic transducers 16 held therein to substantially completely ultrasonically inspect a workpiece 18. The manipulator 14 may also include gimbals 20 or universal joint to which the fixture assembly 10 is attached to facilitate scanning the surface of the workpiece 18.

The immersion type ultrasonic inspection system 12 also includes an immersion tank or reservoir 22 which is filled with water 24 and into which the workpiece 18 is immersed. The water provides improved coupling of the ultrasonic energy or sound waves between the transducers 16 and the workpiece 18.

The system 12 may also include a turntable 26 or fixture arrangement upon which the workpiece 18 may be placed or fixtured, and the turntable 26 may be rotated by the ultrasonic inspection system 12 to facilitate scanning of the flat surfaces of the workpiece 18.

The transducers 16 are electrically coupled by conductors 28 to an ultrasonic fault detector 30, such as a KB-6000™ five-channel multiplexer as manufactured by Krautkramer Branson or the like. The electrical conductors 28 are connected to a multiplexer 32 of the ultrasonic fault detector 30 and the detector 30 also includes a pulser module 34 and a gate module 36. The ultrasonic fault detector 30 will, therefore, generate ultrasonic energy or sound waves which are transmitted to the transducers 16 by the multiplexer 32 and electrical conductors 28 and receives return echoes from any defects or faults in the workpiece 18 via the transducers 16, conductors 28 and the multiplexer 32. Generation of the ultrasonic waves or pulses by pulser module 34 is gated by the gate module 36 to permit receipt of any ultrasonic echoes caused by faults or defects in the workpiece 18 between generation and transmission of each pulse of ultrasonic energy or signals by the detector 30.

The detector 30 is electrically connected to a display 38 which provides a visual image or indication of the fault and facilitates in identification of the location of that fault within the workpiece 18.

Figure 2A:
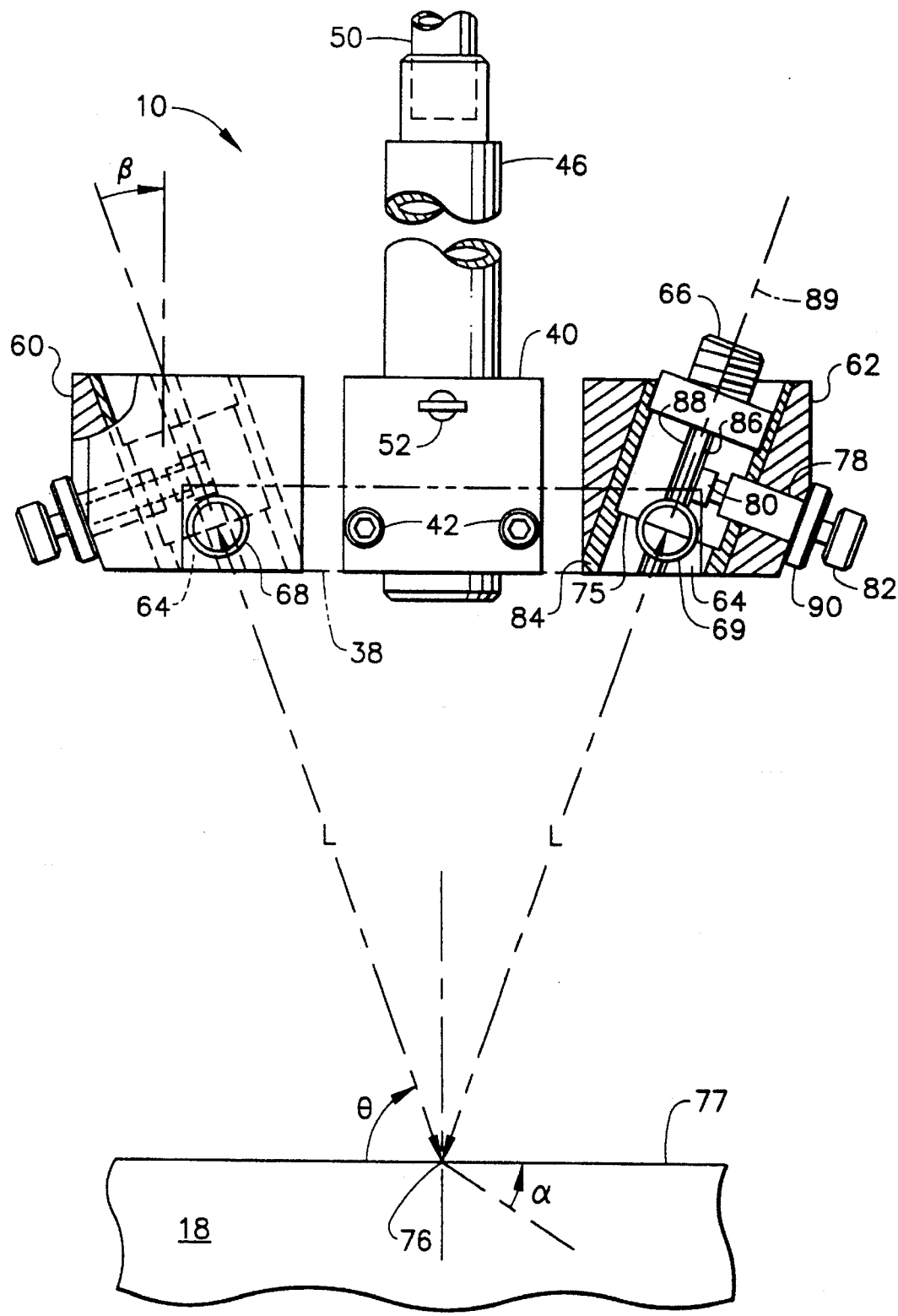
FIG. 2A is a detailed side elevation view of one embodiment of the ultrasonic fixture assembly for holding multiple ultrasonic transducers in accordance with the present invention.
Figure 2B:
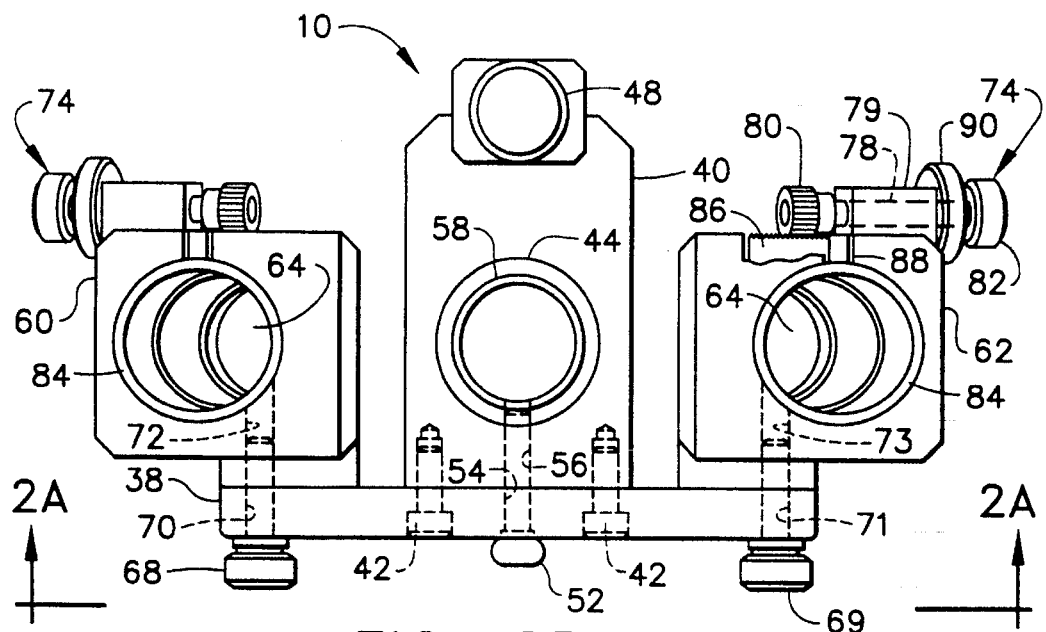
FIG. 2B is a top view of the ultrasonic fixture assembly of FIG. 2A.

Referring to FIGS. 2A and 2B, in accordance with the present invention, the ultrasonic fixture assembly 10 includes an elongated mounting bar 38 and a central transducer mounting block 40 or receptacle mounted in a central location of the elongated mounting bar 38 by fasteners 42. As best shown in FIG. 2B, the central transducer mounting block 40 has a first channel 44 or opening formed therein for slidably receiving a longitudinal wave type ultrasonic transducer 46. The longitudinal wave ultrasonic transducer 46 may be positioned and retained in place by a thumbscrew 52 which is received through a hole 54 formed through the elongated mounting bar 38 and threadedly received in another hole 56 formed through the central mounting block 40 and open to channel 44 to permit tightening of the thumbscrew 52 against a longitudinal wave transducer 46 inserted into the first channel 44. It should be noted that the longitudinal wave transducer 46 can be easily exchanged or replaced by another conventional type transducer if the original transducer fails or if a different type of transducer is desired to be mounted in the fixture assembly 10.

In accordance with the present invention, a sleeve 58 may be disposed within the first channel 44 to accommodate different sizes and types of transducers.

In accordance with the present invention, at least one shear transducer mounting block or receptacle is pivotably mounted to the elongated mounting bar 38 on each side of the central transducer mounting block 40. These shear transducer mounting blocks may be designated as the left hand shear mounting block 60 and the right hand shear mounting block 62. Each of these shear transducer mounting blocks or receptacles 60 and 62 have a channel 64 formed therein for slidably receiving a shearwave type ultrasonic transducer 66. As best shown in FIG. 2A, the channel 64 is formed through the shear mounting block 62 at a predetermined angle β to facilitate injecting or introducing an ultrasonic sound wave or signal transmitted by the transducer 66 into the workpiece 18 at a selected angle of incidence θ to provide a desired angle of refraction α of the ultrasonic sound wave or signal within the workpiece 18 for shearwave ultrasonic inspection of the interior of the workpiece 18.

The shear mounting blocks 60 and 62 are fastened to the elongated mounting bar 38 by respective thumbscrews 68 and 69 which are received through holes 70 and 71 formed through the elongated mounting bar 38 and threadedly received in holes 72 and 73 formed in the shear mounting blocks 60 and 62. The shear transducer mounting blocks 60 and 62 may then be positioned by hand at a predetermined angle relative to the elongated mounting bar 38 and the central transducer mounting block 40 and then held at this selected angle by tightening the respective thumbscrews 68 and 69 to frictionally retain or hold the shear mounting blocks 60 and 62 in the selected position to provide the desired angle of incidence θ of the shearwave ultrasonic signal into the workpiece 18 during an inspection operation.

In accordance with the present invention, an adjustment means 74 is associated with each shear transducer mounting block 60 and 62 for slidably adjusting the position of the shearwave transducer 66 disposed within the channel 64 formed in the transducer mounting blocks 60 and 62 to permit positioning of the shearwave transducer 66 at a predetermined water path length (L) defined as the distance between an operating face 75 of the transducer 66 and the surface 77 of the workpiece 18 under inspection. The water path length (L) adjustment mechanism 74 permits focusing the ultrasonic energy or signal from the shearwave transducers 66 and the longitudinal wave transducer 46 at a desired location or point 76 within the workpiece 18. Those skilled in the art will, therefore, recognize that the present invention is capable of ultrasonically detecting flaws within the workpiece 18 at various angles of orientation relative to the surface 77 of the workpiece 18 without having to perform multiple scans across the workpiece surface 77.

The water path length adjustment mechanism 74 includes a gear shaft 78 retained within a housing 79 and rotatable therein. The housing 79 is mounted to the shear transducer mounting block 60 and 62 or is integrally formed therewith. The gear shaft 78 has a gear spur 80 mounted at one end thereof and a knurled knob 82 mounted at a distal end to permit turning of the gear shaft 78 with the thumb and forefinger.

In accordance with the present invention, a sleeve 84 is slidably received within the channel 64 formed in each of the shear mounting blocks 60 and 62. A rack gear 86 is attached to the sleeve 84 and extends through a longitudinal slot 88 formed in a side of each of the shear transducer mounting blocks 60 and 62. The longitudinal slot 88 and the rack gear 86 extending therethrough are oriented parallel to a centerline 89 of the channel 64 formed in each of the shear transducer mounting blocks 60 and 62. The rack gear 86, the sleeve 84 and the shearwave transducer 66 disposed within the sleeve 84 will then slide within the shear transducer mounting block, either 60 or 62, in response to rotation of the knurled knob 82 to permit positioning of the shearwave transducer 66 at the predetermined water path length (L) prior to an ultrasonic inspection.

A locking nut 90 may be threadedly received on the gear shaft 78 to permit locking the gear shaft 78 in place to prevent rotation thereof during an inspection operation and to retain the water path at the predetermined length (L) during an inspection operation. The gear shaft is retained or locked in position by tightening the locking nut 90 against the housing 79 after the knob 82 is rotated to position the shearwave transducer 66 at the desired position within the channel 64.

Figure 3:
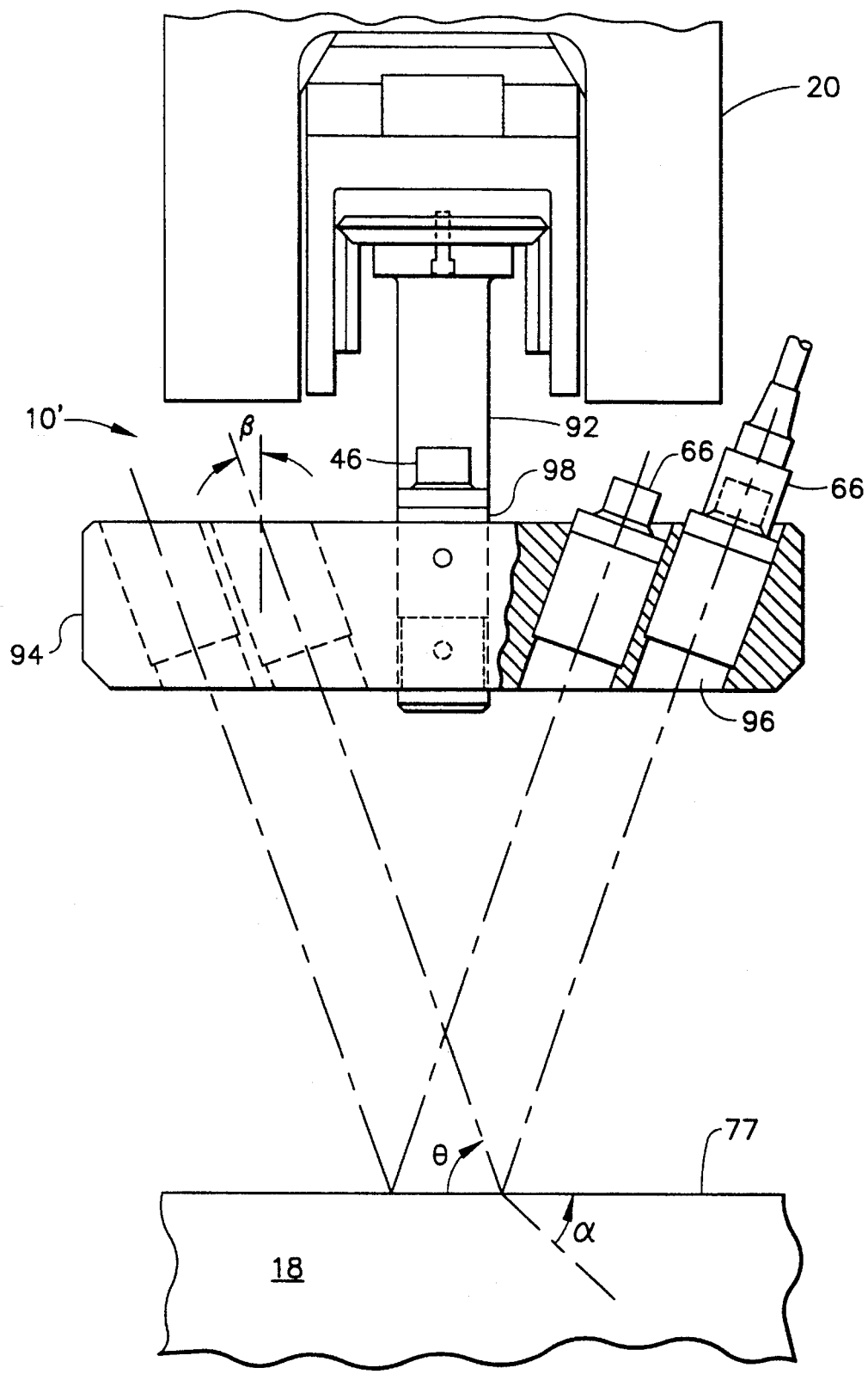
FIG. 3 is a side elevation cross-sectional view of an ultrasonic fixture assembly in accordance with another embodiment of the present invention.

In accordance with another embodiment of the present invention, a plurality of shearwave transducers 66 may be disposed on both sides of the longitudinal wave transducer 46 as shown in FIG. 3. This configuration further reduces the number of scans required to substantially completely inspect the workpiece 18 and permits crisscrossing the ultrasonic sound waves or signals for a more complete inspection.

The ultrasonic fixture assembly 10' includes a central support shaft 92 which is mountable to gimbals 20 or universal joint of the ultrasonic inspection system manipulator 14 (FIG. 1). A transverse shear transducer receiver or mounting support member 94 is mounted to the support shaft 92. The transverse mounting member 94 has a plurality of receptacles or channels 96 formed therein on either side of the central transducer mounting receptacle or channel 98. The channels 96 are preferably formed at a selected angle $\beta$ relative to the longitudinal wave transducer to inject or introduce the shearwave signals into the workpiece at a selected angle of incidence $\theta$ to provide a desired refractive wave angle $\alpha$ within the workpiece 18.

The transverse mounting member 94 could also be formed in individual mounting blocks similar to that shown in FIG. 2A to permit adjustment and preselection of the angle of incidence $\theta$ of the shearwave similar to that described with respect to FIG. 2A. Additionally, the ultrasonic fixture assembly 10' may include a water path adjustment mechanism 74 similar to that described with respect to reference numeral 74 in FIGS. 2A and 2B.

Figure 4B:
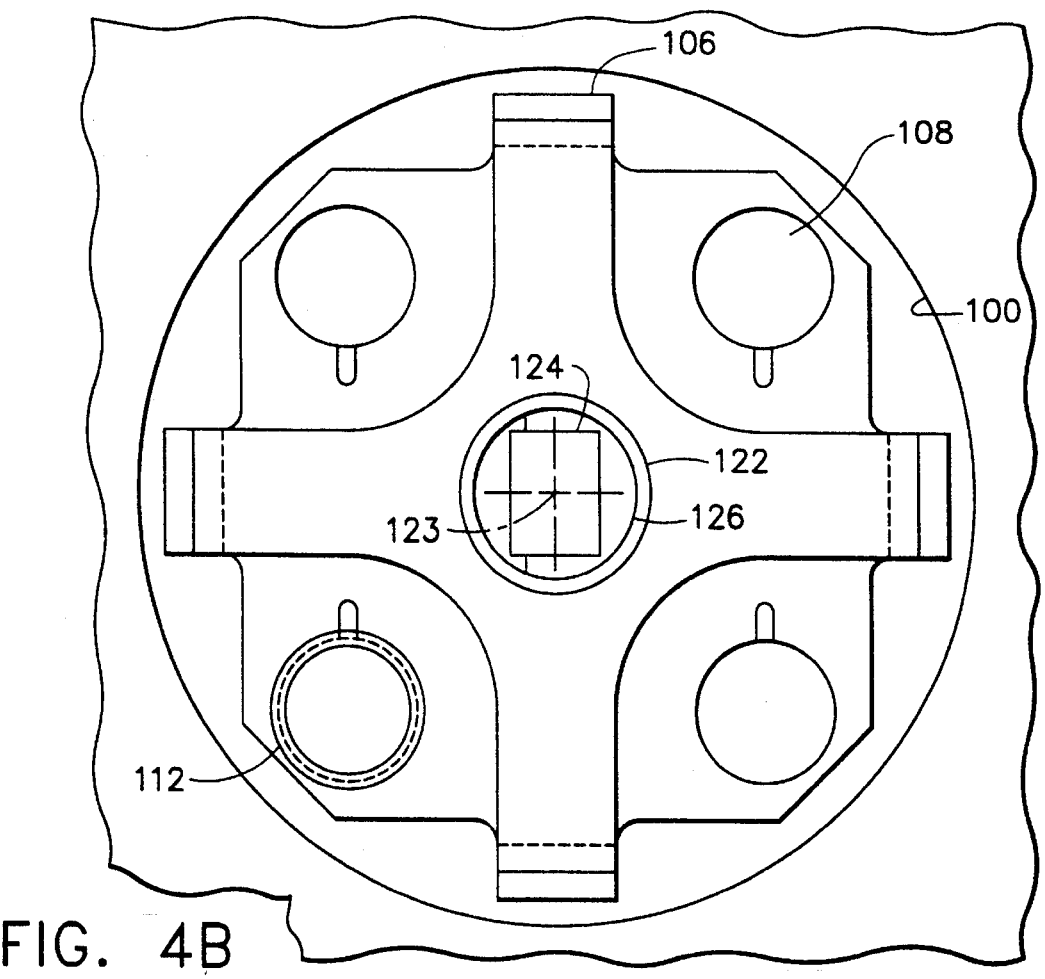
FIG. 4B is a cross-sectional view of the ultrasonic fixture assembly shown in FIG. 4A taken along lines 4B.
Figure 4A:
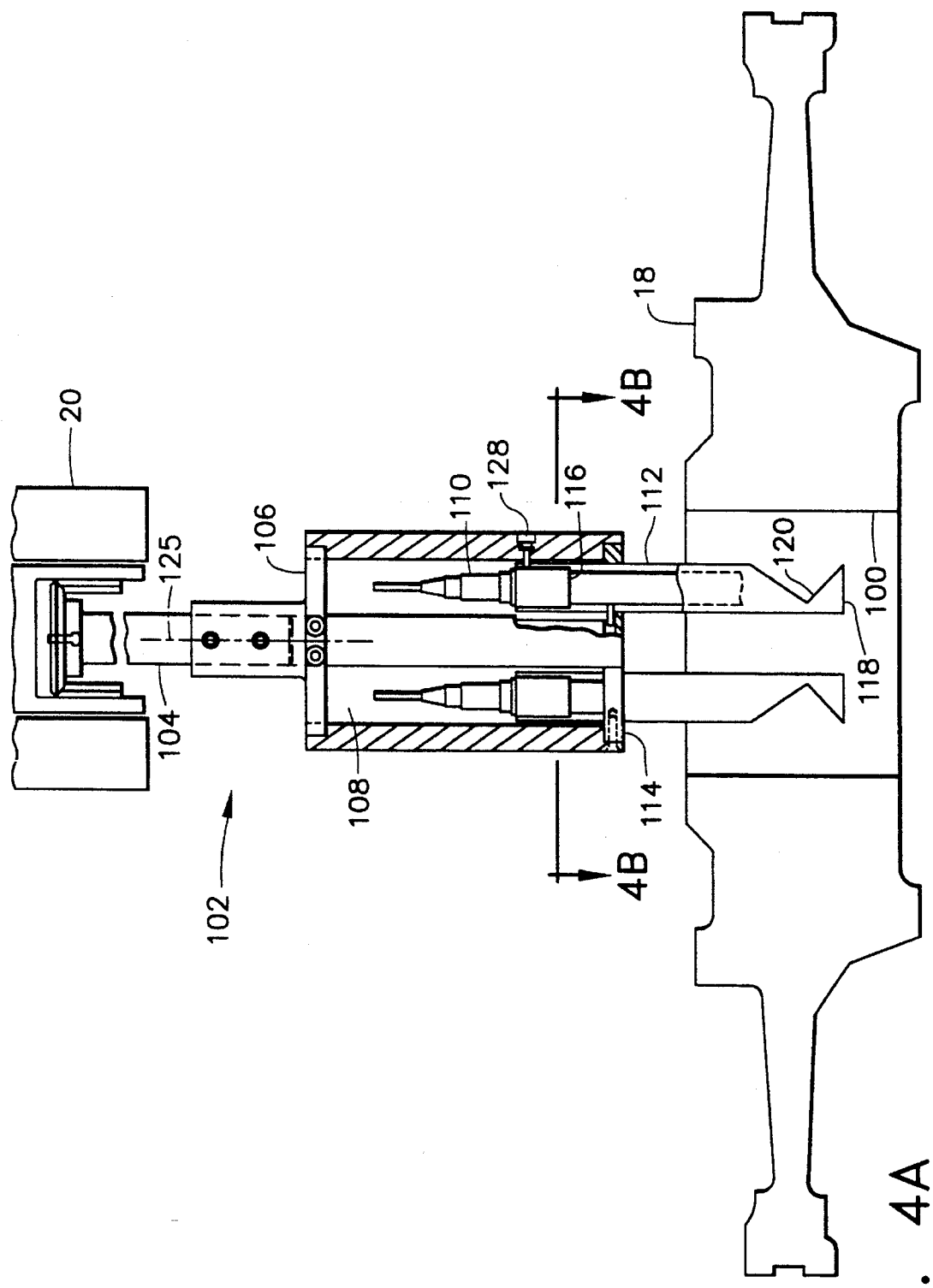
FIG. 4A is a side elevation cross-sectional view of an ultrasonic fixture assembly in accordance with a further embodiment of the present invention for inspecting a bore or channel formed through a workpiece.

A further embodiment of the present invention for inspecting a bore 100 through a workpiece, such as the interior of a hub of a disk 18 for a gas turbine engine or the like, is shown in FIGS. 4A and 4B. The ultrasonic fixture assembly 102 for inspecting the interior of a bore 100 includes a central support rod 104 for attaching the fixture assembly 102 to gimbals 20 or universal joint of the manipulator 14 of an ultrasonic inspection system 12 (FIG. 1). A transducer receiver or support member 106 is attached at one end to the support rod 104 and has a plurality of uniformly, circumferentially spaced receptacles or openings 108, each for respectively receiving a different ultrasonic transducer 110. A tube 112 is respectively slidably received in each of said plurality of openings 108 at an end 114 of the transducer support member 108 opposite to the end at which the central support rod 104 is attached to the transducer support member 106. One end of each of the tubes 112 is coupled to an operating face 116 of the associated ultrasonic transducer 110 and a distal end 118 of the tube 112 has a mirror 120 or reflective device mounted therein at a predetermined angle to reflect the ultrasonic energy or sound waves from the ultrasonic transducer 110 into the workpiece 18 at a selected angle of incidence.

A central receptacle or opening 122 is also formed in the transducer support member 106 for receiving a center ultrasonic transducer 124 (FIG. 4B). A central tube 126 may also be coupled to the central transducer 124. The central opening 122 has a centerline 123 which is aligned with a centerline 125 (FIG. 4A) of the central support rod 104 and the transducer support member 106. The center transducer 124 is then used to align the fixture 102 in a bore 100 of a workpiece 18 to be inspected in proper alignment such that each mirror 120 of the uniformly, circumferentially spaced tubes 112 is spaced at an equal distance from the workpiece 18.

A thumbscrew 128 is associated with each opening 108 in the transducer support member 106 to permit securing each of the transducers 110 and the associated tube 112 in a predetermined position within the transducer support member opening 108.

It will be readily understood by those skilled in the art that the present invention is not limited to the specific embodiments described and illustrated herein. Different embodiments and illustrations besides those shown herein and described as well as variations, modifications and equivalent arrangements will now be apparent or will be reasonably suggested by the foregoing specification and drawings, without departing from the substance or scope of the invention. While the present invention has been described herein in detail in relation to its preferred embodiments, it is to be understood that this disclosure is only illustrative and exemplary of the present invention and is made merely for purposes of providing a full and enabling disclosure of the invention. Accordingly, it is intended that the invention be limited only by the spirit and scope of the claims appended hereto.

What is claimed is:

1. An ultrasonic fixture assembly for holding multiple ultrasonic transducers, comprising:

a central support rod for attaching said fixture assembly to an immersion type ultrasonic inspection manipulator;

a support member attached at one end to said support rod and having a plurality of uniformly, circumferentially spaced openings formed therein, each opening for receiving a respective ultrasonic transducer;

a plurality of tubes each slidably received in a respective one of said plurality of openings at an end of said support member opposite to said one end, one end of each of said plurality of tubes being coupled to an operating end of an associated one of the ultrasonic transducers and a distal end of each of said plurality of tubes having a mirror for reflecting ultrasonic energy from the associated one of the ultrasonic transducers at a predetermined angle into a workpiece under inspection; and a central opening formed in said support member and having a centerline in alignment with a centerline of said central support rod and said support member for receiving a center ultrasonic transducer, the center transducer being used to align said ultrasonic fixture assembly with a bore of a workpiece to be inspected to position each of said mirrors an equal distance from the workpiece.

2. The ultrasonic fixture assembly of claim 1, further comprising means for retaining each of the transducers and said tubes in a predetermined position within each of said tube's respective support member opening.

* * * * *